United States Patent
Czarnecki

(10) Patent No.: US 10,646,412 B1
(45) Date of Patent: May 12, 2020

(54) MICRONIZED COMPOSITE POWDER ADDITIVE

(71) Applicant: Micro Powders, Inc., Tarrytown, NY (US)

(72) Inventor: Richard John Czarnecki, Tarrytown, NY (US)

(73) Assignee: Micro Powders, Inc., Tarrytown, NY (US)

( * ) Notice: Subject to any disclaimer, the term of this patent is extended or adjusted under 35 U.S.C. 154(b) by 1 day.

(21) Appl. No.: 16/379,220

(22) Filed: Apr. 9, 2019

(51) Int. Cl.

| A61K 8/18 | (2006.01) |
| A61K 8/02 | (2006.01) |
| A61K 8/29 | (2006.01) |
| A61K 8/92 | (2006.01) |
| A61Q 17/04 | (2006.01) |
| C09D 7/61 | (2018.01) |
| C09D 7/65 | (2018.01) |
| C09D 5/08 | (2006.01) |
| C09D 7/40 | (2018.01) |

(52) U.S. Cl.
CPC .............. *A61K 8/0245* (2013.01); *A61K 8/29* (2013.01); *A61K 8/92* (2013.01); *A61Q 17/04* (2013.01); *C09D 5/086* (2013.01); *C09D 7/61* (2018.01); *C09D 7/65* (2018.01); *C09D 7/69* (2018.01)

(58) Field of Classification Search
CPC ...................................................... A61K 8/18
See application file for complete search history.

(56) References Cited

U.S. PATENT DOCUMENTS

| 5,028,417 A | 7/1991 | Bhat et al. |
| 5,188,831 A | 2/1993 | Nicoll et al. |
| 5,340,567 A | 8/1994 | Cole et al. |
| 5,498,406 A | 3/1996 | Nearn et al. |
| 7,384,697 B2 | 6/2008 | Chen et al. |
| 7,582,147 B1 | 9/2009 | Parker et al. |
| 2006/0171870 A1 | 8/2006 | Qi et al. |
| 2013/0177616 A1* | 7/2013 | Marim de Olivera ........ A61K 8/0283 424/401 |
| 2016/0053398 A1 | 2/2016 | Kurtz et al. |

FOREIGN PATENT DOCUMENTS

| DE | 3642794 A1 | 6/1987 |
| EP | 0535972 A1 | 4/1993 |
| EP | 0619999 A2 | 10/1994 |
| EP | 0628303 A1 | 12/1994 |
| EP | 0752922 B1 | 1/1997 |
| JP | S5862106 A | 4/1983 |
| JP | 6233219 B2 * | 11/2017 |
| KR | 101648676 B1 | 8/2016 |
| WO | 9006103 A1 | 6/1990 |
| WO | 9311742 A1 | 6/1993 |
| WO | 9641614 A1 | 12/1996 |
| WO | 9703776 | 2/1997 |
| WO | 9707069 A1 | 2/1997 |
| WO | 2013040636 A1 | 3/2013 |
| WO | 2015090622 A1 | 6/2015 |
| WO | 2016013975 A1 | 1/2016 |

* cited by examiner

*Primary Examiner* — Benjamin J Packard
(74) *Attorney, Agent, or Firm* — Whitmyer IP Group LLC

(57) ABSTRACT

A solvent-free composite powder comprising at least one thermoplastic material and at least one submicron nanoparticle material.

27 Claims, 2 Drawing Sheets

MICRONIZED COMPOSITE POWDER ADDITIVE

TECHNICAL FIELD

Figure 1:
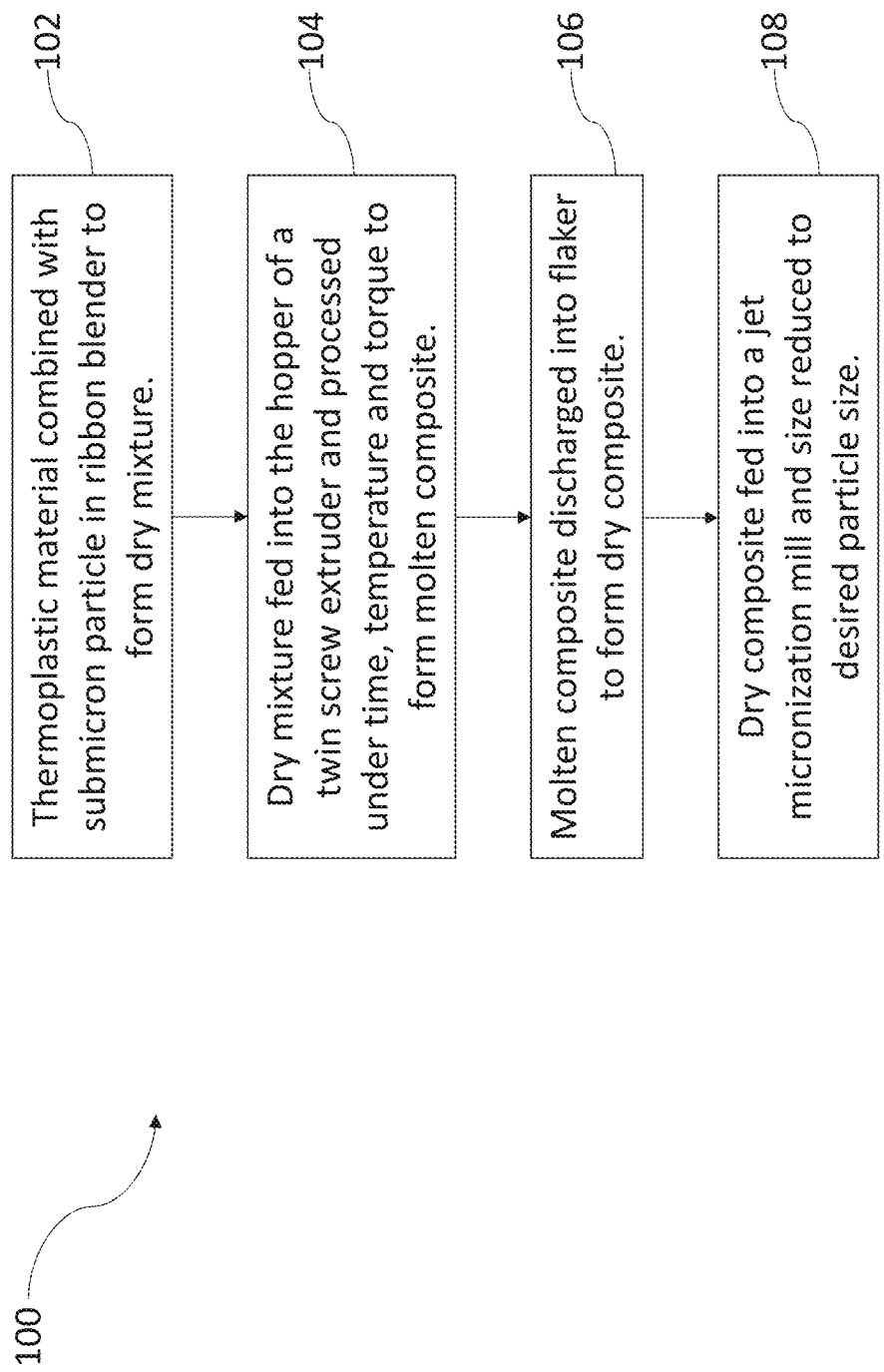

The present invention relates generally to micronized composite powder additives. More specifically, the present invention relates to micronized composite powder additives containing thermoplastic materials and submicron particles and the method to produce those composites.

BACKGROUND

Micronized wax additives have been used to modify coatings for decades. They can provide a wide range of properties, including surface protection, gloss reduction, water repellency, and texturizing. These additives are typically based on low molecular weight polymeric materials, including polyethylene, polypropylene, carnauba wax, and other synthetic and natural materials. Micronized wax additives can also be used in cosmetics and personal care products, providing properties that include dry binding, thickening, mattifying, and texturizing.

Recent years have witnessed unprecedented growth of research and applications in the area of nanoscience and nanotechnology. Recent leaps in areas such as microscopy have given scientists new tools to understand and take advantage of phenomena that occur naturally when matter is organized at the nanoscale. In essence, these phenomena are based on "quantum effects" and other physical effects such as expanded surface area. In addition, a majority of biological processes occur at the nanoscale which gives scientists models and templates to imagine and construct new processes that can enhance their work in medicine, imaging, computing, printing, chemical catalysis, materials synthesis, and many other fields. Nanotechnology is not simply working at ever smaller dimensions; rather, working at the nanoscale enables scientists to utilize unique physical, chemical, mechanical, and optical properties of materials. In particular, metal nanoparticles exhibit interesting electronic magnetic and catalytic properties that are not present in the bulk metal. These materials offer exciting opportunities to develop smarter, more functional additives.

During the last few years, research on toxicologically relevant properties of engineered nanoparticles has increased tremendously. A number of international research projects and additional activities are ongoing in the EU and the US, nourishing the expectation that more relevant technical and toxicological data will be published. Their widespread use allows for potential exposure to engineered nanoparticles during the whole lifecycle of a variety of products. When looking at possible exposure routes for manufactured nanoparticles, inhalation, dermal and oral exposure are the most obvious, depending on the type or product in which nanoparticles are used. Studies show that nanoparticles can deposit in the respiratory tract after inhalation. For a number of nanoparticles, oxidative stress-related inflammatory reactions have been observed. Tumor-related effects have only been observed in rats, and might be related to overload conditions.

There are also a few reports that indicate uptake of nanoparticles in the brain via the olfactory epithelium. Nanoparticle translocation into the systemic circulation may occur after inhalation but conflicting evidence is present on the extent of translocation. These findings urge the need for additional studies to further elucidate these findings and to characterize the physiological impact. There is currently little evidence from skin penetration studies that dermal applications of metal oxide nanoparticles used in sunscreens lead to systemic exposure. However, the question has been raised whether the usual testing with healthy, intact skin will be sufficient. Uptake of nanoparticles in the gastrointestinal tract after oral uptake is a known phenomenon, of which use is intentionally made in the design of food and pharmacological components.

Only a few specific nanoparticles have been investigated in a limited number of test systems and extrapolation of this data to other materials is not possible. Air pollution studies have generated indirect evidence for the role of combustion derived nanoparticles (CDNP) in driving adverse health effects in susceptible groups. Experimental studies with some bulk nanoparticles (carbon black, titanium dioxide, iron oxides) that have been used for decades suggest various adverse effects. However, engineered nanomaterials with new chemical and physical properties are being produced constantly and the toxicity of these is unknown. Therefore, despite the existing database on nanoparticles, no blanket statements about human toxicity can be given at this time. In addition, limited ecotoxicological data for nanomaterials precludes a systematic assessment of the impact of nanoparticles on ecosystems.

When particle sizes of solid matter in the visible scale are compared to what can be seen in a regular optical microscope, there is little difference in the properties of the particles. But when particles are created with submicron dimensions (especially in the range of 1-100 nanometers where the particles can be "seen" only with powerful specialized microscopes), the materials' properties change significantly from those at larger scales. This is the size of scale where so-called quantum effects rule the behavior and properties of particles. Properties of materials are size-dependent in this scale range. Thus, when particle size is made to be nanoscale, properties such as melting point, fluorescence, electrical conductivity, magnetic permeability, and chemical reactivity change as a function of the size of the particle.

Many benefits of nanotechnology depend on the fact that it is possible to tailor the structures of materials at extremely small scales to achieve specific properties, thus greatly extending the materials science toolkit. Using nanotechnology, materials can effectively be made stronger, lighter, more durable, more reactive, more sieve-like, or better electrical conductors, among many other traits. Many everyday commercial products are currently on the market and in daily use that rely on nanoscale materials and processes.

Nanoscale additives to or surface treatments of fabrics can provide lightweight ballistic energy deflection in personal body armor, or can help them resist wrinkling, staining, and bacterial growth.

Clear nanoscale films on eyeglasses, computer and camera displays, windows, and other surfaces can make them water- and residue-repellent, antireflective, self-cleaning, resistant to ultraviolet or infrared light, antifog, antimicrobial, scratch-resistant, or electrically conductive.

Nanoscale materials are beginning to enable washable, durable "smart fabrics" equipped with flexible nanoscale sensors and electronics with capabilities for health monitoring, solar energy capture, and energy harvesting through movement.

Nano-bioengineering of enzymes as aiming to enable conversion of cellulose from wood chips, corn stalks, unfertilized perennial grasses, etc., into ethanol for fuel. Cellulosic nanomaterials have demonstrated potential applications in a wide array of industrial sectors, including electronics, construction, packaging, food, energy, health care, automotive, and defense. Cellulosic nanomaterials are projected to be less expensive than many other nanomaterials and, among other characteristics, tout an impressive strength-to-weight ratio.

Nano-engineered materials in automotive products include high-power rechargeable battery systems, thermoelectric materials for temperature control, tires with lower rolling resistance, high-efficiency/low-cost sensors and electronics, thin-film smart solar panels, and fuel additives for cleaner exhaust and extended range.

Nanostructured ceramic coatings exhibit much greater toughness than conventional wear-resistant coatings for machine parts. Nanotechnology-enabled lubricants and engine oils also significantly reduce wear and tear, which can significantly extend the lifetimes of moving parts in everything from power tools to industrial machinery.

Nanoparticles are used increasingly in catalysis to boost chemical reactions. This reduces the quantity of catalytic materials necessary to produce desired results, saving money and reducing pollutants. Two big applications are in petroleum refining and in automotive catalytic converters.

Nano-engineered materials make superior household products such as degreasers and stain removers, environmental sensors, air purifiers, and filters, antibacterial cleansers, and specialized paints and sealing products, such a self-cleaning house paints that resist dirt and marks.

Nanoscale materials are also being incorporated into a variety of personal care products to improve performance. Nanoscale titanium dioxide and zinc oxide have been used for years in sunscreen to provide protection from the sun while appearing invisible on the skin.

It is evident from these many examples that the power of nanoscale materials presents many opportunities to create innovative products. The challenge is to harness the power of the nanoparticle in such a way that the shortcomings of these novel materials are avoided.

Nanoparticles, having an extremely high surface areas, are very difficult to disperse or otherwise incorporate into a liquid system, whether it's water based, solvent based, oil based, or other. Nanoparticles are difficult to handle in both laboratory and industrial processes, as they can create fine clouds of dust when conveyed, dispensed, or otherwise incorporated into a product. Nanoparticles are still not fully understood with regards to potential risks to human health on exposure including, but not limited to inhalation and skin absorption. Nanoparticles can abrade, wear, or otherwise degrade manufacturing, processing, and filling equipment.

Submicron particles (including nanoparticles) can be classified into different types according to the size, morphology, physical and chemical properties. Some of them are carbon-based particles, ceramic particles, metal particles, semiconductor particles, and polymeric particles.

Carbon-based nanoparticles include two main materials: carbon nanotubes (CNTs) and fullerenes. CNTs are nothing but graphene sheets rolled into a tube. These materials are mainly used for the structural reinforcement as they are 100 times stronger than steel. CNTs can be classified into single-walled carbon nanotubes (SWCNTs) and multi-walled carbon nanotubes (MWCNTs). CNTs are unique in a way as they are thermally conductive along the length and non-conductive across the tube. Fullerenes are the allotropes of carbon having a structure of hollow cage of sixty or more carbon atoms. The structure of C-60 is called Buckminsterfullerene, and looks like a hollow football. The carbon units in these structures have a pentagonal and hexagonal arrangement. These have commercial applications due to their electrical conductivity, structure, high strength, and electron affinity. Graphene particles are known to provide benefits that include corrosion resistance and electrostatic dissipation (ESD).

Ceramic particles are inorganic solids made up of oxides, carbides, carbonates and phosphates. These submicron particles and/or nanoparticles have high heat resistance and chemical inertness. They have applications in photocatalysis, photodegradation of dyes, drug delivery, and imaging. By controlling some of the characteristics of ceramic nanoparticles like size, surface area, porosity, surface to volume ratio, etc, they perform as a good drug delivery agent. These nanoparticles have been used effectively as a drug delivery system for a number of diseases like bacterial infections, glaucoma, cancer, etc.

Metal particles are prepared from metal precursors. These submicron particles and/or nanoparticles can be synthesized by chemical, electrochemical, or photochemical methods. Metal nanoparticles, such as aluminum oxide, are also highly effective at improving surface durability properties (scratch resistance, abrasion resistance, etc.) in coatings.

Inorganic particles can include titanium dioxide submicron and/or nanoparticles, which can impart a self-cleaning effect to glass and solid exterior surfaces. Zinc oxide particles have been found to have superior UV blocking properties compared to its bulk substitute.

Semiconductor nanoparticles have properties like those of metals and non-metals. They are found in the periodic table in groups II-VI, III-V, or IV-VI. These particles have wide bandgaps, which on tuning shows different properties. They are used in photocatalysis, electronics devices, photo-optics and water splitting applications. Some examples of semiconductor nanoparticles are GaN, GaP, InP from group III-V, ZnO, ZnS, CdS, CdSe, CdTe are II-VI semiconducts and silicon and germanium are from group IV.

Polymeric submicron and/or nanoparticles are organic based particles. Depending upon the method of preparation, these can have structures shaped like nanocapsular or nanospheres. A nanosphere particle has a matrix-like structure whereas the nanocapsular particle has core-shell morphology. In the former, the active compounds and the polymer are uniformly dispersed whereas in the latter the active compounds are confined and surrounded by a polymer shell. Some of the merits of polymeric nanoparticles are controlled release, protection of drug molecules, ability to combine therapy and imaging, specific targeting and many more. They have applications in drug delivery and diagnostics. The drug deliveries with polymeric nanoparticles are highly biodegradable and biocompatible.

A limitation of the commercial industrial use of submicron particles is that they are highly difficult to disperse. These powders have very high surface areas, and it is challenging to use these powders in additives without preliminary processing. This could include chemical surface modification, to stabilize the particle in a liquid media, and wet phase agitation bead milling, to separate, wet, and disperse the powder into its primary particle size. When wet processing is used, the choice of processing media limits the versatility of the modified powder. For example, nanoparticles can be dispersed with sufficient time and energy into a solvent based polyurethane medium, but the resulting dispersion would not be suitable for end uses in water based, energy curable, or 100% solids applications. Other processing aids such as surfactants and dispersants may need to be incorporated, further limiting the versatility of the dispersion.

Therefore, it would be desirable to find a way to deliver the performance of these submicron particles in a dry matrix that is readily dispersible into a wide variety of end systems without the use of a solvent, using much easier and common mixing technology. It would be further desirable to develop a composition containing submicron particles that are safe to handle.

SUMMARY

The needs set forth herein as well as further and other needs and advantages are addressed by the present embodiments, which illustrate solutions and advantages described below.

The present inventor has discovered that the inherent performance features of the submicron particles are maintain when incorporated into a micronized thermoplastic composite.

The present inventor has also discovered that these thermoplastic composites are significantly easier to disperse into all types of systems, including, but not limited to, industrial coatings (water-based, solvent-based, and UV curable), cosmetics, and personal care products.

The present inventor has also discovered novel methods for incorporating submicron particles into micronized thermoplastics. A benefit of this approach versus prior art is that no solvents are used in the process. Residual solvents can limit the use of the particle in sensitive applications that include food packaging and personal care products.

An additional benefit of the invention is that the potential health and safety concerns with the handling, breathing, ingesting, or touching submicron and/or nanoparticles is avoided with a submicron thermoplastic composite powder.

A further benefit of the invention is that the submicron thermoplastic composite powder demonstrates a reduction tendency to degrade processing equipment and machinery. Many submicron powders are extremely hard and durable, and can damage steel and other processing surfaces. When combined in a composite particle with a lubricating thermoplastic material, this abrasive effect is reduced.

The powder of one embodiment, according to the present teaching, include composite particles, and said composite particles comprise at least one thermoplastic material and at least on submicron nanoparticle material. The at least one thermoplastic material comprises from about 50 to 99 weight percent of said powder. The at least one submicron nanoparticle material comprises from about 1 to 50 weight percent of said powder. The powder is solvent-free.

In a further embodiment, the at least one thermoplastic material is a polymer, plastic, or wax, which can be melted and reformed.

In a further embodiment, the at least one submicron nanoparticle material is a nano-aluminum oxide, nano-titanium oxide, or a nano-graphene oxide.

In a further embodiment, the at least one submicron particle has a mean particle size below 1,000 nm.

In a further embodiment, the composite powder has a maximum particle size below 1,000 microns.

In a further embodiment, the composite powder has a mean particle size ranging from 0.1 to 44 microns.

The composite powder of another embodiment, according to the present teaching, includes, but is not limited to, at least one thermoplastic material and at least one submicron particle, wherein the composite powder is solvent free.

In a further embodiment, the composite powder has a maximum particle size below 1,000 microns.

In a further embodiment, the composite powder has a mean particle size ranging from 0.1 to 44 microns.

In a further embodiment, the at least one submicron particle has a mean particle size below 1,000 nm.

In a further embodiment, the at least one thermoplastic material is a polymer, plastic, or wax which can be melted down and reformed.

In a further embodiment, the at least one submicron particle is nano aluminum oxide.

In a further embodiment, the composite powder with the nano aluminum oxide submicron particle is used as a coating additive to improve surface durability.

In a further embodiment, the at least one submicron particle is nano titanium oxide.

In a further embodiment, the composite powder with the nano titanium oxide submicron particle is used as an additive in personal care products to improve SPF protection.

In a further embodiment, the at least one submicron particle is graphene oxide.

In a further embodiment, the composite powder with the graphene oxide submicron particle is used as an additive to improve corrosion resistance in a surface coating.

In a further embodiment, the composite powder with the graphene oxide submicron particle is used as an additive to improve electrostatic dissipation in a surface coating.

The powder of another embodiment, according to the present teaching, include composite particles, and said composite particles comprise at least one thermoplastic material and at least on submicron nanoparticle material. The at least one thermoplastic material comprises from about 50 to 99 weight percent of said powder. The at least one submicron nanoparticle material comprises from about 1 to 50 weight percent of said powder. The powder is solvent-free. The powder is produced by dry mixing, melting, cooling, pelletizing, and compressing said composite particles into said powder.

Other embodiments of the system and method are described in detail below and are part of the present teachings.

For a better understanding of the present embodiments, together with other and further aspects thereof, reference is made accompanying drawings and detailed description, and its scope will be pointed out in the appended claims.

BRIEF DESCRIPTION OF THE DRAWINGS

FIG. 1 is a schematic flow diagram illustrating a method of producing the composite powder.

FIG. 2 is a schematic flow diagram illustrating another method of producing the composite powder.

DETAILED DESCRIPTION

The present teachings are described more fully hereinafter with reference to the accompanying drawings, in which the present embodiments are shown. The following description is presented for illustrative purposes only and the present teachings should not be limited to these embodiments.

In compliance with the statute, the present teachings have been described in language more or less specific as to structural and methodical features. It is to be understood, however, that the present teachings are not limited to the specific features shown and described, since the systems and methods herein disclosed comprise preferred forms of putting the present teachings into effect.

For purposes of explanation and not limitation, specific details are set forth such as particular architectures, interfaces, techniques, etc. in order to provide a thorough understanding. In other instances, detailed descriptions of well-known devices, circuits, and methods are omitted so as not to obscure the descriptions with unnecessary detail.

In this invention, "thermoplastic material" is broadly defined as any substance (such as, but not limited to, polymer, plastic, natural wax) that can be melted, liquefied, softened, or otherwise modified such that it can be homogenously combined with the submicron or nanoscale material, solidified, and micronized into a fine powder. Examples include, but are not limited to, polymers including polyethylene, polypropylene, polyamide, polyester, natural waxes such as carnauba wax, and synthetic waxes such as Fischer-Tropsch wax.

In this invention, "submicron nanoparticle material" is defined as a particle with a mean particle size below 1,000 nm. Preferably, the submicron nanoparticle material is below 500 nm. Most preferably, the submicron nanoparticle material is below 100 nm.

In this invention, the composite powder has a maximum particle size below 1,000 microns. Preferably, the composite powder has a mean particle size ranging from 0.1 to 44 microns. More preferably, the composite powder has a mean particle size of 5-20 microns with a maximum particle size of 44 microns. Most preferably, the composite powder has a mean particle size of 8 to 12 microns with a maximum particle size of 31 microns.

In this invention, sufficient time is defined as a time long enough to homogenize the submicron nanoparticle material with the thermoplastic material matrix to form a molten composite.

In this invention, sufficient temperature is defined as a temperature high enough to convert the dry mixture into the molten composite.

In this multi-step process, the thermoplastic material is selected to serve as the matrix for the composite powder. This thermoplastic material can then be melted and combined with the submicron nanoparticle material using sufficient energy to wet, separate, and disperse the submicron nanoparticle materials homogenously throughout the thermoplastic material matrix. This thermoplastic composite can then be size reduced and supplied as an easy to disperse powder.

In the first step the thermoplastic material component(s) are first combined with the submicron and/or nanoscale material by melt mixing, extrusion, or other processes familiar to those skilled in the art. In the second step, this thermoplastic composite material is size reduced using air micronization (irregular fine particles), mechanical milling (irregular coarse particles), spray melt congealing (spherical coarse and/or fine particles) or other processes familiar to those skilled in the art. In the case of spray melt congealing, the two steps can be combined. The result is a micronized thermoplastic composite powder that no longer contains free submicron or nanoscale material. This affords the ability to incorporate submicron and/or nanoscale materials into a wide range of products without the complexity, risks, and difficulties long associated with the use of these materials.

Referring now to FIG. 1, the figure shows, by way of a non-limiting example, a schematic flow diagram illustrating a method of producing the composite powder 100. In the first step, the thermoplastic material is combined with the submicron nanoparticle material(s) in a ribbon blender to form a dry mixture 102. In the second step, the dry mixture is fed into the hopper of a twin screw extruder and processed under sufficient time, temperature and torque to form a molten composite 104. In the third step, the molten composite is discharged into a flaker to form a dry composite 106. In the last step, the dry composite is fed into a jet micronization mill and the size is reduced to desired particle size 108.

Figure 2:
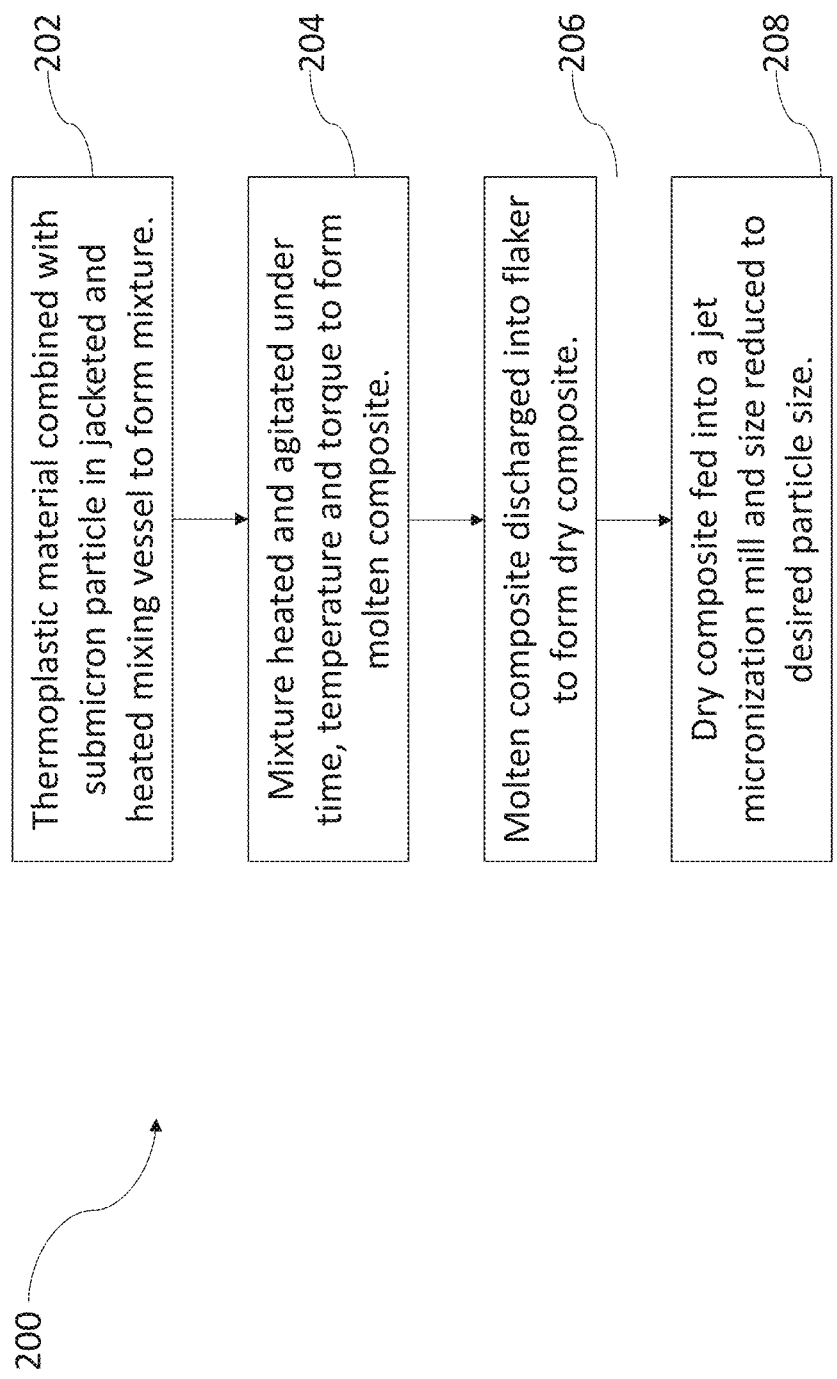

Referring now to FIG. 2, the figure shows, by way of non-limiting example, a schematic flow diagram illustrating another method of producing the composite powder 200. In the first step, the thermoplastic material combined with the submicron nanoparticle material(s) in a jacketed and heated mixing vessel to form a dry mixture 202. In the second step, the dry mixture is heated and agitated under sufficient time, temperature and torque to form a molten composite 204. In the third step, the molten composite is discharged into a flaker to form a dry composite 206. In the last step, the dry composite is fed into a jet micronization mill and the size is reduced to desired particle size 208.

EXAMPLES OF COMPOSITE POWDERS

Example 1

Aluminum Oxide/Polyethylene/PTFE Micronized Thermoplastic Material Nanocomposite
Step 1:
The following components are combined using extrusion melt mixing:
85% polyethylene wax (molecular weight approximately 2,000)
15% polytetrafluoroethylene (mean particle size 4.0 µm)
5% fumed aluminum oxide (primary particle size between 7-40 nm).
Step 2:
The composite material from Step 1 is cooled, crushed, and micronized, using a jet mill, to a mean particle size (my) of 3.5-5.5 µm and a maximum particle size (D100) of 15.56 µm.

This composite powder is useful to improve scratch and abrasion resistance when used as an additive in industrial paints, inks, and coatings.

Example 2

Titanium Dioxide/Synthetic Wax Micronized Thermoplastic Composite
Step 1:
The following components are combined using extrusion melt mixing:
95% synthetic wax (molecular weight approximately 1,100)
5% 15 nm titanium dioxide
Step 2:
The composite material from Step 1 is cooled, crushed, and micronized, using a jet mill, to a mean particle size (mv) of 8.0-12.0 µm and a maximum particle size (D100) of 31.11 µm.

This composite powder is useful as an SPF booster when formulated into skin creams and lotions.

Example 3

Polypropylene/Graphene Oxide Micronized Thermoplastic Composite
Step 1:
The following components are combined using extrusion melt mixing:
50% polypropylene wax (molecular weight approximately 10,000)

50% graphene oxide (nominal particle size of 400 nm, 90% of particles below 800 nm in diameter)

Step 2:

The composite material from Step 1 is cooled, crushed, and micronized, using a jet mill, to a mean particle size (mv) of 10-12 µm and a maximum particle size (D100) of 31.11 µm.

This composite powder is useful at improving corrosion resistance when used as an additive in coatings applied to steel and other metal surfaces.

In all three examples the composite powder can be produced using various methods.

In one method the thermoplastic solid material (in the form of flakes, pellets, etc.) are physically combined with the submicron nanoparticle material in a ribbon blender or other suitable dry blending machine. The dry mixture is fed into the hopper of a horizontal twin screw extruder, and processed under time, temperature, and torque conditions suitable to homogenously disperse the submicron particle in the molten thermoplastic. The molten composite is discharged into a flake, pellet, or prill. This dry composite material is fed into a jet micronization mill and size reduced to the desired particle size (mean and maximum size).

In another method the thermoplastic solid material (in the form of flakes, pellets, etc.) are physically combined with the submicron nanoparticle materials in a jacketed and heated mixing vessel equipped with agitation. The dry mixture is gradually heated to melt the polyethylene, and is then agitated under sufficient time, temperature, and torque, to homogenously disperse the submicron particle in the molten thermoplastic. The molten composite is discharged onto a flaker belt or through and priller or pelletizer, to form a flake, pellet, or prill. This dry composite material is fed into a jet micronization mill and size reduced to the desired particle size (mean and maximum size).

In this second method after the mixture is heated and agitated, the molted mixture is sprayed through a fine orifice into a cooling tower, where the molten composite exits the orifice, cools, and forms a spherical particle. The particles can be further size classified using screens or other techniques to refine the particle size distribution. The molten composite is sufficiently cooled when the molten composite becomes a hard and tack free solid such as a flake, prill, or pellet.

While the present teachings have been described above in terms of specific embodiments, it is to be understood that they are not limited to these disclosed embodiments. Many modifications and other embodiments will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

What is claimed is:

1. A powder comprising:
   homogenous composite particles;
   said homogenous composite particles comprising at least one thermoplastic material and at least one submicron nanoparticle material;
   wherein said at least one thermoplastic material comprises from about 50 to 99 weight percent of said powder;
   wherein said at least one submicron nanoparticle material comprises from about 1 to 50 weight percent of said powder;
   wherein said powder is solvent-free.

2. The powder of claim 1, wherein said at least one thermoplastic material is a polymer, plastic, or wax, which can be melted and reformed.

3. The powder of claim 2, wherein said at least one submicron nanoparticle material is a nano-aluminum oxide, nano-titanium oxide, or a nano-graphene oxide.

4. The powder of claim 1, wherein said at least one submicron nanoparticle material has a mean particle size below 1,000 nm.

5. The powder of claim 1, wherein said homogenous composite powder has a maximum particle size below 1,000 microns.

6. The powder of claim 1, wherein said homogenous composite powder has a mean particle size ranging from 0.1 to 44 microns.

7. A composite powder comprising:
   at least one thermoplastic material; and
   at least one submicron nanoparticle material;
   wherein said at least one submicron nanoparticle material is dispersed in said at least one thermoplastic material homogenously.

8. The composite powder of claim 7, wherein said composite powder has a maximum particle size below 1,000 microns.

9. The composite powder of claim 7, wherein said composite powder have a mean particle size ranging from 0.1 to 44 microns.

10. The composite powder of claim 7, wherein said at least one submicron nanoparticle material has a mean particle size below 1,000 nm.

11. The composite powder of claim 7, wherein said at least one thermoplastic material is a polymer, plastic, or wax, which can be melted and reformed.

12. The composite powder of claim 11, wherein said at least one submicron nanoparticle material is a nano aluminum oxide.

13. The composite powder of claim 12, wherein said composite powder is used as a coating additive to improve surface durability.

14. The composite powder of claim 7, wherein said at least one submicron nanoparticle material is a nano titanium oxide.

15. The composite powder of claim 14, wherein said composite powder is used as an additive in personal care products to improve SPF protection.

16. The composite powder of claim 7, wherein said at least one submicron nanoparticle material is a graphene oxide.

17. The composite powder of claim 16, wherein said composite powder is used as an additive to improve corrosion resistance in a surface coating.

18. The composite powder of claim 16, wherein said composite powder is used as an additive to improve electrostatic dissipation in a surface coating.

19. A powder comprising:
   homogenous composite particles;
   said homogenous composite particles comprising at least one thermoplastic material and at least one submicron nanoparticle material;
   wherein said at least one thermoplastic material comprises from about 50 to 99 weight percent of said powder;
   wherein said at least one submicron nanoparticle material comprises from about 1 to 50 weight percent of said powder;

wherein said powder is produced by dry mixing, melting, cooling, pelletizing, and compressing said composite particles.

20. The powder of claim 19, wherein said at least one thermoplastic material is a polymer, plastic, or wax, which can be melted and reformed.

21. The powder of claim 19, wherein said at least one submicron nanoparticle material is a nano-aluminum oxide, nano-titanium oxide, or a nano-graphene oxide.

22. The powder of claim 19, wherein said at least one submicron nanoparticle material has a mean particle size below 1,000 nm.

23. The powder of claim 19, wherein said homogenous composite powder has a maximum particle size below 1,000 microns.

24. The powder of claim 19, wherein said homogenous composite powder has a mean particle size ranging from 0.1 to 44 microns.

25. The powder of claim 1, wherein said at least one submicron nanoparticle material has a mean particle size below 500 nm.

26. The powder of claim 7, wherein said at least one submicron nanoparticle material has a mean particle size below 500 nm.

27. The powder of claim 19, wherein said at least one submicron nanoparticle material has a mean particle size below 500 nm.

* * * * *